US006873405B2

(12) United States Patent
Kido et al.

(10) Patent No.: US 6,873,405 B2
(45) Date of Patent: Mar. 29, 2005

(54) PROPAGATION MEASURING APPARATUS AND A PROPAGATION MEASURING METHOD

(75) Inventors: Takashi Kido, Tokyo (JP); Shoji Niki, Tokyo (JP)

(73) Assignee: Advantest Corporation, Tokyo (JP)

( * ) Notice: Subject to any disclaimer, the term of this patent is extended or adjusted under 35 U.S.C. 154(b) by 0 days.

(21) Appl. No.: 10/740,999

(22) Filed: Dec. 19, 2003

(65) Prior Publication Data

US 2004/0130725 A1 Jul. 8, 2004

Related U.S. Application Data

(63) Continuation of application No. PCT/JP02/06175, filed on Jun. 20, 2002.

(30) Foreign Application Priority Data

Jul. 2, 2001 (JP) ....................................... 2001-200377

(51) Int. Cl.[7] ................................................ G01J 1/00
(52) U.S. Cl. ..................... 356/121; 250/214.1; 359/180
(58) Field of Search ........................ 356/121, 317–319, 356/326, 483–484, 478–479; 250/214.1, 227.19; 359/180–182, 278, 160, 156

(56) References Cited

U.S. PATENT DOCUMENTS

| 5,150,248 | A | * | 9/1992 | Alfano et al. ................ 398/147 |
| 5,256,968 | A | * | 10/1993 | Loualiche et al. ............. 324/96 |
| 6,144,679 | A | * | 11/2000 | Herman et al. ................ 372/21 |
| 6,348,683 | B1 | * | 2/2002 | Verghese et al. .......... 250/214.1 |
| 6,525,862 | B2 | * | 2/2003 | Fisher et al. ................. 359/278 |
| 6,563,622 | B2 | * | 5/2003 | Mueller et al. .............. 398/182 |
| 6,661,519 | B2 | * | 12/2003 | Fukasawa .................... 356/432 |
| 6,738,397 | B2 | * | 5/2004 | Yamamoto et al. ............ 372/21 |
| 6,747,736 | B2 | * | 6/2004 | Takahashi .................... 356/319 |

FOREIGN PATENT DOCUMENTS

| JP | 2-150747 | 6/1990 |
| JP | 2000-121550 | 4/2000 |
| JP | 2001-21503 | 1/2001 |

OTHER PUBLICATIONS

S. Matsuura et al., "A Tunable Cavity–Locked Diode Laser Source for Terahertz Photomixing," IEEE Transactions of Microwave Theory and Techniques; Mar. 2000, vol. 48, No. 3, pp. 380–387.
S. Matsuura et al., "High–Resolution Terahertz Spectroscopy by a Compact Radiation Source Based on Photomixing with Diode Lasers in a Photoconductive Antenna," Journal of Molecular Spectroscopy, 1998nen, vol. 187, pp. 97–101.
Int'l. Search Report issued in Int'l. Application No. PCT/JP02/06175 mailed Jul. 30, 2002, 2 pgs.
"The Frontiers of Information and Communication Research, All of Communications Research Laboratory"; (The third chapter: The Exploitation of Frequency Resources, 10 TerahertzElectronics; Dempa Shimbun–sha) (7 pgs.).
"Chromatic Dispersion Measurement Over A 100km Dispersion–Shifted Single–Mode Fibre by a New Phase–Shift Technique" vol. 22, No. 11, May 22, 1986; Electronics Letters; pp. 570–572 (3 pgs.).
Shiro Ryu, et al.; "Novel Chromatic Dispersion Measurement Method Over Continuous Gigahertz Tuning Range"; Journal of Lightwave Technology, vol. 7, No. 8, Aug. 1989; pp. 1177–1180; IEEE (4 pgs.).

* cited by examiner

*Primary Examiner*—Gregory J. Toatley, Jr.
*Assistant Examiner*—Sang H. Nguyen
(74) *Attorney, Agent, or Firm*—Osha & May L.L.P.

(57) ABSTRACT

A propagation measuring apparatus for measuring propagation characteristics of an object to be measured includes a first light source for outputting a first optical signal of a first frequency, a second light source for outputting a second optical signal of a second frequency, a terahertz light outputting unit for generating terahertz light of a frequency, which is equal to a difference between the first and second frequencies, by using the first and second optical signals and radiating the terahertz light to the object to be measured, a first detecting unit for detecting the terahertz light passing through the object to be measured and a measuring unit for measuring the propagation characteristics of the object to be measured based on the terahertz light detected by the first detecting unit.

3 Claims, 11 Drawing Sheets

PROPAGATION MEASURING APPARATUS AND A PROPAGATION MEASURING METHOD

The present application is a continuation application of PCT/JP02/06175 filed on Jun. 20, 2002 which claims priority from a Japanese patent application No. 2001-200377 filed on Jul. 2, 2001, the entire contents of which are incorporated herein by reference.

BACKGROUND OF THE INVENTION

1. Technical Field

The present invention relates to a propagation measuring apparatus and a propagation measuring method.

2. Related Art

Recently, the art of measuring propagation characteristics of an object in a terahertz light area (about 100 GHz~10 THz) has been noted.

FIG. 9 shows a conventional propagation measuring apparatus 200 schematically. The propagation measuring apparatus 200 measures the propagation characteristics of an object by using femtosecond optical pulses, i.e., extremely short optical pulses whose pulse width is femtosecond-order. In addition, the art is written in, e.g., "The Frontiers of Information and Communication Research, All of Communications Reseach Laboratory" (The third chapter: The Exploitation of Frequency Resources, 10 Terahertz Electronics; Dempa Shimbun-sha).

In the propagation measuring apparatus 200, a femtosecond light pulse 110 of, e.g., less than 100 femtoseconds outputted from a pulse laser is split by a beam splitter 112. One of the femtosecond pulse 110 split by the beam splitter 112 is inputted into a terahertz electromagnetic wave transmitter 118 as a trigger pulse 114. The other one is inputted into a terahertz electromagnetic wave receiver 122 as a sampling pulse 116. The sampling pulse 116 is delayed properly by a time delay means 120.

The terahertz electromagnetic wave transmitter 118 is configured by forming a parallel transmission line 124 functioning as an antenna as well onto a light conductive film (not shown) made of low temperature grown gallium arsenide. The light conductive film made of low temperature grown gallium arsenide has excellent characteristics, in which the optical response speed is extremely high.

In a state where the terahertz electromagnetic wave transmitter 118 is applied with direct current voltage 126, when the trigger pulse 114 of, e.g., less than 100 femto seconds is incident into a gap part of the parallel transmission line 124, the parallel transmission line 124 is short-circuited temporarily, and thus a precipitous change in current occurs. Accordingly, terahertz pulses including frequency components of about 100 GHz to a few THz are transmitted from the antenna of the terahertz electromagnetic wave transmitter 118.

The terahertz pulse transmitted from the terahertz electromagnetic wave transmitter 118 is focused by off-axis parabolic mirrors 128 and incident into the sample 130. The terahertz pulse passing through the sample 130 is forced by off-axis parabolic mirrors 128 and incident into the terahertz electromagnetic wave receiver 122.

As the terahertz electromagnetic wave receiver 122, a device such as the terahertz electromagnetic wave transmitter 118 is used. The terahertz electromagnetic wave receiver 122 samples the terahertz electromagnetic wave incident into the gap part of the parallel transmission line 132 functioning as an antenna by using the sampling pulse 116. The signal obtained by the terahertz electromagnetic wave receiver 122 is amplified by a current amplifier 134.

The propagation measuring apparatus 200 detects the waveform of the terahertz pulse excited from the terahertz electromagnetic wave transmitter 118 while changing the delay time of the sampling pulse 116. In the propagation measuring apparatus 200 the waveform of the terahertz pulse is detected in relation to the delay time. The terahertz pulse detected in this way is coherent in a broadband and includes information relating to amplitude and phase, so it is useful for examining the physical characteristics of the sample 130. In addition, by measuring the sample 130 being moved in X-Y directions it is possible to visualize the physical characteristics of the sample.

In addition, a wavelength dispersion measuring apparatus for measuring and obtaining the wavelength dispersion of an object to be measured in regard to the close infrared light area is proposed.

FIG. 10 shows a conventional wavelength dispersion measuring apparatus 300 schematically. Further, the art of this is written in S. Ryu, Y. Horiuchi and K. Mochizuki, "Novel chromatic dispersion measurement method over continuous Gigahertz tuning range", J. Lightwave Technol., Vol.7, No.8, pp.1177~1180, 1989 or M. Fujise, M. Kuwazuru, M. Nunokawa and Y. Iwamoto, "Chromatic dispersion measurement over a 100-km dispersion-shifted single-mode fibre by a new phase-shift technique", Electron. Lett., Vol. 22, No.11, pp.570~572, 1986.

In the wavelength dispersion measuring apparatus 300, the laser light of the close infrared light area outputted from a wavelength variable light source 210 is inputted into an optical intensity modulator 212. The optical intensity modulator 212 modulates the intensity of the laser light outputted from the wavelength variable light source 210 with a sine wave by using a reference signal of frequency $f_{IF}$ supplied from a high frequency reference signal source 214.

The laser light modulated by the optical intensity modulator 212 is incident into an object to be measured 216. The laser light passing through the object to be measured 216 is detected by a photoelectric converter 218, converted into an electrical signal and amplified by an amplifier 220. The detected signal amplified by the amplifier 220 is inputted into a phase-amplitude comparator 224 of a network analyzer 222.

The phase-amplitude comparator 224 compares the detected signal amplified by the amplifier 220 with the reference signal supplied from the high frequency reference signal source 214. The comparison result by the phase-amplitude comparator 224 is converted by an A/D converter 226. And, a group delay time is obtained by a data processing block 228 as below.

The group delay time $\tau(\lambda_i)$ is represented by:

$$\tau(\lambda_i) = \phi(\lambda_i, f_{IF})/(2\pi f_{IF}),$$

wherein, the wavelength of the laser light outputted from the wavelength variable light source 210 is $\lambda_i$, the frequency of the reference signal supplied from the high frequency reference signal source 214 is $f_{IF}$ and the phase obtained by the phase-amplitude comparator 224 is $\phi(\lambda_i, f_{IF})$.

Therefore, by performing the measurement as above while changing the wavelength $\lambda_i$ of the laser light outputted from the wavelength variable light source 210 continuously, the group delay time $\tau(\lambda_i)$ can be obtained for each wavelength. In addition, the wavelength dispersion $D(\lambda_i)$, which is the differentiation of the group delay time $\tau(\lambda_i)$ with respect to the wavelength, is represented by:

$$D(\lambda_i)=\Delta\tau(\lambda_i)/\Delta\lambda_i,$$

wherein $\Delta\tau(\lambda_i)=\tau(\lambda_{i+1})-\tau(\lambda_i)$ and $\Delta\lambda_i=\lambda_{i+1}-\lambda_i$.

In addition, the method for obtaining the group delay time $\tau(\lambda_i)$ as above is called the phase shift method.

In the wavelength dispersion measuring apparatus 300 it is possible to measure the group delay time $\tau(\lambda_i)$ by using the phase analysis art of high frequency, so that the measurement of the wavelength dispersion can be performed with high precision.

In addition, an apparatus for obtaining an optical tomographic image of an object to be measured with the heterodyne detection is proposed.

FIG. 11 shows a conventional apparatus for obtaining an optical tomographic image 400 schematically. Further, the art of this is disclosed in Japanese Patent Application Publications Nos. 1990-150747 and 2000-121550.

In the apparatus for obtaining an optical tomographic image 400, a laser light outputted from a laser light source 310 is focused by lenses 312 and 314 and split by a beam splitter 316.

One of the laser light split by the beam splitter 316 is irradiated to an object to be measured 318. The laser light passing through the object to be measured 318 is reflected by a mirror 320 and incident into a beam splitter 322.

The other laser light split by the beam splitter 316 is reflected by a mirror 324 and inputted into a light frequency converter 326. The light frequency converter 326 converts the frequency of the laser light by using a reference signal supplied from a high frequency reference signal source 328. The laser light whose frequency has been converted by the light frequency converter 326 is incident into the beam splitter 322.

In the beam splitter 322, the laser light passing through the object to be measured 318 and the laser light whose frequency has been converted by the light frequency converter 326 are merged. The laser light merged by the beam splitter 322 is incident into a light detector 324.

The light detector 324 detects the light by using the heterodyne detection. In the heterodyne detection, there is directivity, so that only the direct component of the laser light passing through the object to be measured 318 is detected.

The light detected by the light detector 324 is demodulated by a demodulator 326 and analyzed by a computer 329. The analysis result by the computer 329 is displayed as a tomographic image by an image display device 330.

The principle of the apparatus for obtaining an optical tomographic image 400 is shown below.

The electric field $e_1(t)$ of the light incident into the object to be measured 318 and the electric field $e_2(t)$ of the light outputted from the light frequency converter 326 are respectively represented by:

$$e_1(t)=A_1 \cos \omega_C t$$

and $$e_2(t)=A_2 \cos \{(\omega_C+p)t+\theta_2\},$$

wherein $A_1$ and $A_2$ are the electric field strengths, p is the shift amount of the angular frequency of the light, $\theta_2$ is a constant phase and $\omega_C$ is the angular frequency of the light.

In addition, the transfer function $Y(\omega_C)$ of the object to be measured 318 is represented by:

$$Y(\omega_C)=Y_0\exp(j\phi_0),$$

then the electric field ed incident into the light detector 324 is represented by:

$$e_d=Y(\omega_C)A_1 \cos \omega_C t+A_2 \cos \{(\omega_C+p)t+\theta_2\} \text{ and}$$

the output current $i_d$ of the light detector 324 is represented by:

$$i_d=\alpha\{Y_0^2 A_1^2+A_2^2+2Y_0 A_1 A_2 \cos(pt+\theta_2-\phi_0)\},$$

wherein $\alpha$ is the proportional coefficient, $\phi_0$ is the phase and $\omega_C$ is the angular frequency of the light. In addition, among the phase $\phi_0$, the angular frequency of the light $\omega_C$, the frequency the group delay time $\tau(\omega_C)$ there is a relation as follows:

$$\tau(\omega_C)=\delta\phi_0/\delta\omega_C.$$

According to the apparatus for obtaining an optical tomographic image 400, by the principle above it is possible to image the tomogram of the object to be measured.

However, in the propagation measuring apparatus 200 shown in FIG. 9, since the propagation characteristics of the sample 130 is measured by using the femtosecond light pulse alone, it is impossible to measure the frequency dependence of the propagation characteristics of the sample 130 in regard to the terahertz light area in detail. Moreover, in the propagation measuring apparatus 200 shown in FIG. 9, the light source generating the femtosecond pulse 110 is of a large scale, and it lacks the stability of, the pulse width or the optical intensity. Further, since the propagation characteristics of the sample 130 is measured while changing the delay time of the sampling pulse 116 gradually, it takes a long time to perform the measurement. In addition, due to using the spatial light, the apparatus becomes large and complicated, so it lacks the stability. Moreover, since the time delay means 120 changes the delay time by using a movable stage, it is affected by the mechanical precision of the movable stage and it is not necessary to be able to perform the measurement with high precision.

In addition, in case of applying the art of the wavelength dispersion measuring apparatus 300 shown in FIG. 10 to the terahertz light area, it is necessary to use a broadband optical intensity modulator of the terahertz light area as the optical intensity modulator 212. However, since the broadband optical intensity modulator of the terahertz light area is not widely spread, it is difficult to procure it and its price is high.

Moreover, in case of applying the art of the wavelength dispersion measuring apparatus 300 shown in FIG. 10 to the terahertz light area, the terahertz light outputted from the wavelength variable light source 210 is inputted into the photoelectric converter 218 via the optical intensity modulator 212 and the object to be measured 216. The transmission technique by which the loss in regard to the terahertz light area is low has not yet been progressed, it is necessary to make the intensity of the terahertz light outputted from the wavelength variable light source 210 large as much as the transmission loss. Therefore, it is necessary to use the wavelength variable light source 210 whose output is great, and thus it becomes an obstacle to making the apparatus small.

In addition, in case of applying the art of the apparatus for obtaining an optical tomographic image 400 shown in FIG. 11 to the terahertz light area, it is necessary to use a broadband light frequency converter of the terahertz light area as the light frequency converter 326. However, since the broadband light frequency converter of the terahertz light area is not widely spread, it is difficult to procure it and its price is high.

In addition, in case of applying the art of the apparatus for obtaining an optical tomographic image 400 shown in FIG. 11 to the terahertz light area, the terahertz light outputted from the laser light source 310 is inputted into the photoelectric converter 324 via the lenses 312 and 314, the beam splitters 316 and 322, the object to be measured 318, the light frequency converter 326, the mirrors 320 and 324. The transmission technique by which the loss in regard to the terahertz light area is low has not yet been progressed, it is necessary to make the intensity of the terahertz light outputted from the laser light source 310 large as much as the transmission loss. Therefore, it is necessary to use the laser light source 310 whose output is great, and thus it becomes an obstacle to making the apparatus small.

In addition, in case of applying the art of the apparatus for obtaining an optical tomographic image 400 shown in FIG. 11 to the terahertz light area, the path of the terahertz light lies on both the object to be measured 318 side and the light frequency converter 326 side, so the optical axis adjustment is complicated.

In addition, since the art of the apparatus for obtaining an optical tomographic image 400 shown in FIG. 11 is to measure only the amplitude without performing any phase comparison, the transmission delay time of the object to be measured 318 cannot be measured, and only the amplitude information such as transmission attenuation can be measured.

SUMMARY OF THE INVENTION

Accordingly, it is an object of the present invention to provide a propagation measuring apparatus and a propagation measuring method, which is capable of overcoming the above drawbacks accompanying the conventional art. The above and other objects can be achieved by combinations described in the independent claims. The dependent claims define further advantageous and exemplary combinations of the present invention.

In order to solve the problems above, according to the first aspect of the present invention, a propagation measuring apparatus for measuring propagation characteristics of an object to be measured includes a first light source for outputting a first optical signal of a first frequency, a second light source for outputting a second optical signal of a second frequency, a terahertz light outputting unit for generating terahertz light of a frequency, which is equal to a difference between the first and second frequencies, by using the first and second optical signals and radiating the terahertz light to the object to be measured, a first detecting unit for detecting the terahertz light passing through the object to be measured and a measuring unit for measuring the propagation characteristics of the object to be measured based on the terahertz light detected by the first detecting unit.

The first and second light sources may output the first and second optical signals of infrared light respectively.

The propagation measuring apparatus may further include a reference signal source for generating a reference signal and a modulating unit for modulating at least one of the first and second optical signals based on the reference signal generated by the reference signal source, wherein the measuring unit may measure the propagation characteristics of the object to be measured based on at least one of the first and second optical signals modulated by the modulating unit and the reference signal generated by the reference signal source.

The modulating unit may modulate the intensity of the first optical signal outputted by the first light source, and the terahertz light outputting unit may generate the terahertz light by using the first optical signal of which the intensity is modulated by the modulating unit and the second optical signal outputted by the second light source and radiate the terahertz light to the object to be measured.

The propagation measuring apparatus may further include a first multiplexer for multiplexing the first optical signal generated by the first light source and the second optical signal generated by the second light source, wherein the modulating unit may modulate the intensities of the first and second optical signals multiplexed by the first multiplexer, and the terahertz light outputting unit may generate the terahertz light by using the first and second optical signals of which the intensities is modulated by the modulating unit and radiate the terahertz light to the object to be measured.

The propagation measuring apparatus may further include a second detecting unit for the terahertz light radiated by the terahertz light outputting unit not through the object to be measured, wherein the measuring unit may measure the propagation characteristics of the object to be measured based on the terahertz light detected by the first and second detecting units.

The propagation measuring apparatus may further include a first demultiplexer for demultiplexing the first optical signal outputted by the first light source, a second demultiplexer for demultiplexing the second optical signal outputted by the second light source, a first multiplexer for multiplexing a first component of the first optical signal demultiplexed by the first demultiplexer and a first component of the second optical signal demultiplexed by the second demultiplexer and a second multiplexer for multiplexing a second component of the first optical signal demultiplexed by the first demultiplexer and a second component of the second optical signal demultiplexed by the second demultiplexer, wherein the terahertz light outputting unit may generate the terahertz light by using the first and second optical signals multiplexed by the first multiplexer and radiate the terahertz light to the object to be measured, the modulating unit may modulate a frequency of the second component of the first optical signal demultiplexed by the first demultiplexer, the second multiplexer may multiplex the second component of the first optical signal of which the frequency is modulated by the modulating unit and the second component of the second optical signal demultiplexed by the second demultiplexer, and the first detecting unit may perform heterodyne detection of the terahertz light passing through the object to be measured by using the second components of the first and second optical signals multiplexed by the second multiplexer.

The propagation measuring apparatus may further include a delay element for delaying at least one of the second component of the first optical signal demultiplexed by the first demultiplexer and the second component of the second optical signal demultiplexed by the second demultiplexer.

The propagation measuring apparatus may further include a second detecting unit for detecting the terahertz light radiated by the terahertz light outputting unit not through the object to be measured and performing heterodyne detection by using the second components of the first and second optical signals multiplexed by the second multiplexer, wherein the measuring unit may measure the propagation characteristics of the object to be measured based on results of the heterodyne detection of the first and second detecting units.

The modulating unit may be an optical intensity modulator, optical frequency converter or acousto-optic converter.

The difference between the first and second frequencies is within a range of 100 GHz to 10 THz, and the terahertz light outputting unit may generate terahertz light of 100 GHz to 10 THz and radiate the terahertz light to the object to be measured.

The first or second light source may sweep frequency and output the first or second optical signal.

The first and second light sources may output the first and second optical signals of continuous light.

According to the second aspect of the present invention, a propagation measuring method for measuring propagation characteristics of an object to be measured includes a first output step of outputting a first optical signal of a first frequency, a second output step of outputting a second optical signal of a second frequency, a terahertz light output step of generating terahertz light of a frequency, which is equal to a difference between the first and second frequencies, by using the first and second optical signals and radiating the object to be measured, a first detection step of detecting the terahertz light passing through the object to be measured and a measurement step of measuring the propagation characteristics of the object to be measured based on the terahertz light detected in the first detection step.

The propagation measuring method may further include a reference signal generation step of generating a reference signal; and a modulation step of modulating at least one of the first and second optical signals based on the reference signal generated in the reference signal generation step, wherein the measurement step may include a step of measuring the propagation characteristics of the object to be measured based on at least one of the first and second optical signals modulated in the modulation step and the reference signal generated in the reference signal.

The propagation measuring method may further include a second detection step of detecting the terahertz light radiated in the terahertz light output step not through the object to be measured, wherein the measurement step may include a step of measuring the propagation characteristics of the object to be measured based on the terahertz light detected in the first and second detection steps.

DETAILED DESCRIPTION OF THE INVENTION

The invention will now be described based on the preferred embodiments, which do not intend to limit the scope of the present invention, but exemplify the invention. All of the features and the combinations thereof described in the embodiment are not necessarily essential to the invention.

[First Embodiment]

Figure 1:
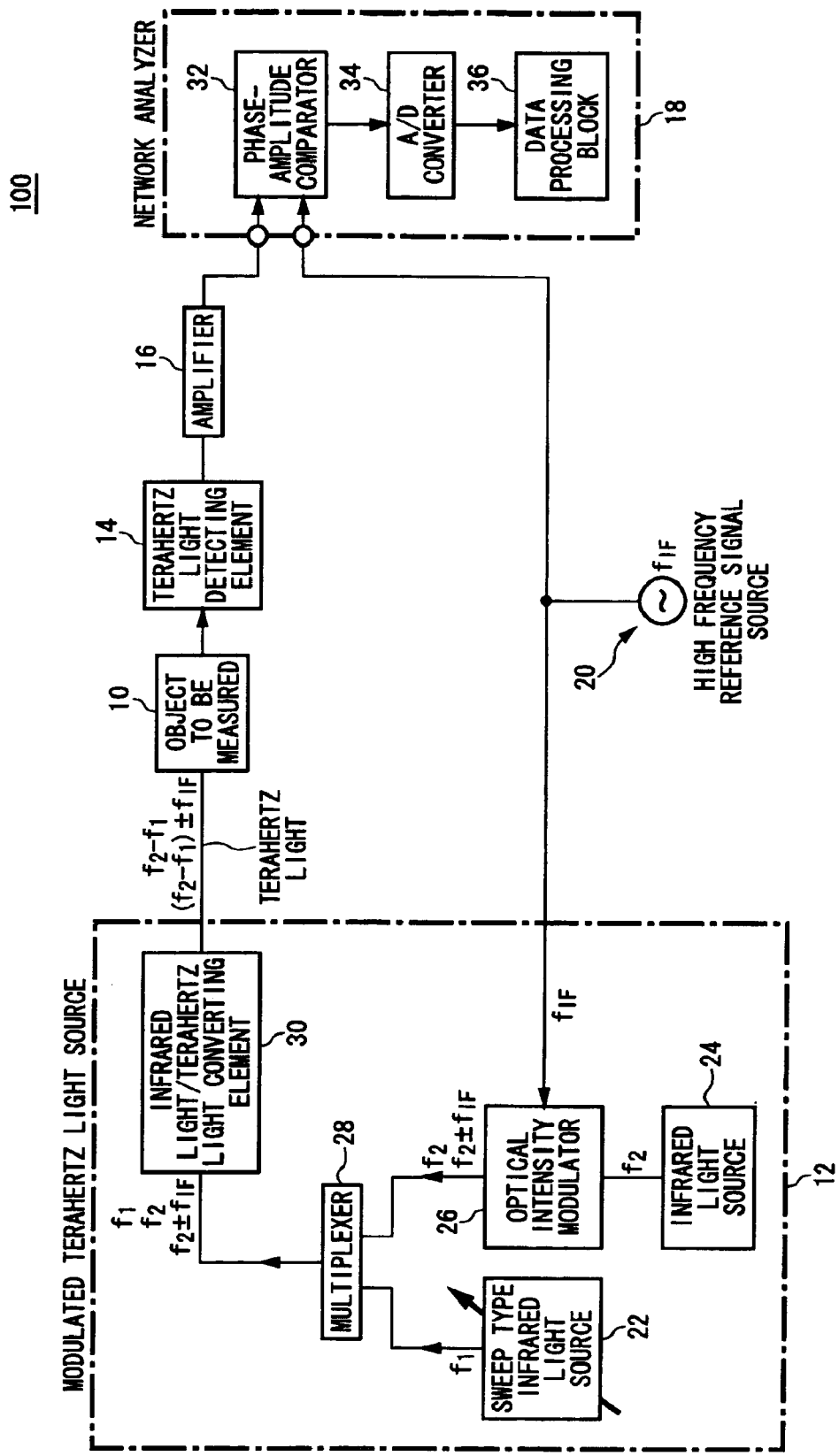
FIG. 1 shows an example of the functional configuration of a propagation measuring apparatus 100 according to a first embodiment of the present invention.

FIG. 1 shows an example of the functional configuration of a propagation measuring apparatus 100 according to a first embodiment of the present invention. The propagation measuring apparatus 100 according to the present embodiment includes a modulated terahertz light source 12 for radiating modulated terahertz light to an object to be measured 10, a terahertz light detecting element 14 that is an example of a first detecting unit for detecting the terahertz light passing through the object to be measured 10, an amplifier 16 for amplifying the detected signal obtained by the terahertz light detecting element 14, a high frequency reference signal source 20 that is an example of a reference signal source for supplying a reference signal to the modulated terahertz light source 12 and a network analyzer 18 and the network analyzer 18 that is example of a measuring unit for analyzing the detected signal amplified by the amplifier 16 and measuring the propagation characteristics of the object to be measured 10.

The terahertz light passing through the object to be measured 10 includes information about the propagation characteristics such as attenuation or delay occurring when passing through the object to be measured 10. Therefore, by detecting and analyzing the terahertz light passing through the object to be measured 10, it is possible to measure the propagation characteristics such as the attenuation or transmission delay in regard to the object to be measured 10.

Hereinafter, each part of the propagation measuring apparatus 100 according to the present embodiment will be described in detail.

(a) The Modulated Terahertz Light Source 12

The modulated terahertz light source 12 includes a sweep type infrared light source 22 that is an example of a first light source for outputting infrared light of frequency $f_1$, an infrared light source 24 that is an example of a second light source for outputting infrared light of frequency $f_2$, an optical intensity modulator 26 that is an example of a modulating unit for modulating the intensity of the infrared light of frequency $f_2$ outputted by the infrared light source 24 by using the reference signal of frequency $f_{IF}$ generated by the high frequency reference signal source 20, a multiplexer 28 for multiplexing the infrared light outputted by the sweep type infrared light source 22 and the infrared light outputted by the optical intensity modulator 26 and an infrared light/terahertz light converting element 30 that is an example of a terahertz light outputting unit for generating and radiating the modulated terahertz light to the object to be measured 10 by using the infrared light multiplexed by the multiplexer 28. In addition, the terahertz light means the light of the terahertz light area, i.e. the light of about 100 GHz to 10 THz.

The sweep type infrared light source 22 outputs continuous light (a continuous wave) of frequency $f_1$. And, the sweep type infrared light source 22 sweeps the frequency $f_1$ and outputs the infrared light. The range of the frequency $f_1$ swept by the sweep type infrared light source 22 is preferably 190 THz to 200 THz. The sweep type infrared light source 22 supplies the outputted infrared light to the multiplexer 28.

The infrared light source 24 outputs continuous light (a continuous wave) of frequency $f_2$. The frequency $f_2$ of the infrared light outputted by the infrared light source 24 is set in order that the difference between the frequencies $f_1$ and $f_2$ ($f_1-f_2$ or $f_2-f_1$) can be within a terahertz area (about 100 GHz to 10 THz). The frequency $f_2$ of the infrared light outputted from the infrared light source 24 is preferably 189.9 THz. The infrared light source 24 supplies the outputted infrared light to the optical intensity modulator 26.

The optical intensity modulator 26 adjusts the intensity of the infrared light of frequency $f_2$ outputted by the infrared light source 24 by using the reference signal of frequency $f_{IF}$ generated by the high frequency reference signal source 20. As the optical intensity modulator 26, e.g. an optical intensity modulator of the infrared light area within 190 THz+5 THz can be used. The optical intensity modulator 26 of the narrowband infrared light area is widely spread, so that it can be procured easily. Therefore, by using the optical intensity modulator 26 of the infrared light area easily available, it is possible to configure the modulated terahertz light source 12 at a low cost.

The optical intensity modulator 26 outputs the infrared light of frequency $f_2 \pm f_{IF}$ whose intensity has been modulated by the optical intensity modulator 26 using the reference signal and the infrared light of frequency $f_2$ whose intensity has not been modulated, and supplies it to the multiplexer 28.

The multiplexer 28 multiplexes the infrared light outputted by the sweep type infrared light source 22 and the infrared light outputted by the optical intensity modulator 26 in order that the polarization directions match each other. And, the multiplexer 28 outputs the combination of the infrared light of frequency $f_1$, the infrared light of frequency $f_2$ and the infrared light of frequency $f_2 \pm f_{IF}$, and supplies it to the infrared light/terahertz light converting element 30.

The infrared light/terahertz light converting element 30 generates the terahertz light modulated by using the infrared light outputted by the multiplexer 28 and radiates it to the object to be measured 10 via an antenna (not shown). The infrared light/terahertz light converting element 30 is configured by forming a parallel transmission line (not shown) functioning as the antenna as well on a light conductive film (not shown) made of, e.g. low temperature grown gallium arsenide. In the light conductive film made of low temperature grown gallium arsenide the optical response speed is extremely high, and it has excellent characteristics. The parallel transmission line is applied with direct current voltage properly. The infrared light/terahertz light converting element 30 can convert the infrared light into the terahertz light with high efficiency.

When the infrared light/terahertz light converting element 30 is supplied with the combination of the infrared light of frequency $f_1$, the infrared light of frequency $f_2$ and the infrared light of frequency $f_2 \pm f_{IF}$ from the multiplexer 28, it performs infrared light/terahertz light conversion. And, the infrared light/terahertz light converting element 30 generates the terahertz light of a frequency of the difference between frequencies of the infrared light supplied, i.e. the terahertz light of frequency $f_2-f_1$ and the terahertz light of frequency $(f_2-f_1) \pm f_{IF}$, and radiates it to the object to be measured 10. Here, $f_2 > f_1$. The infrared light/terahertz light converting element 30 generates the terahertz light of 100 GHz to 10 THz and radiates it to the object to be measured 10.

The terahertz light outputted by the infrared light/terahertz light converting element 30 is equivalent to the terahertz light of frequency $f_2-f_1$ modulated with the reference signal of frequency $f_{IF}$. In other word, according to the modulated terahertz light source 12 of the present embodiment, it is possible to generate the modulated terahertz light by using the optical intensity modulator 26 of the infrared light area without using a broadband optical intensity modulator of the terahertz light area.

In addition, by sweeping the frequency $f_1$ of the infrared light outputted by the sweep type infrared light source 22, the value of $f_2-f_1$ is changed. Therefore, by sweeping the frequency $f_1$ of the infrared light outputted by the sweep type infrared light source 22, it is possible to change the frequencies $f_2-f_1$ and $(f_2-f_1) \pm f_{IF}$ of the terahertz light outputted by the modulated terahertz light source 12 properly.

(b) The Terahertz Light Detecting Element 14

The terahertz light detecting element 14 detects the terahertz light passing through the object to be measured 10 via an antenna (not shown). As the terahertz light detecting element 14, a device such as the infrared light/terahertz light converting element 30 can be used.

The terahertz light detecting element 14 detects the terahertz light of frequency $f_2-f_1$ radiated by modulated terahertz light source 12 and attenuated and delayed when passing through the object to be measured 10 and the terahertz light of frequency $(f_2-f_1) \pm f_{IF}$. And, the terahertz light detecting element 14 outputs the detected signal including the information about the propagation characteristics of the object to be measured 10 in the electrical signal form, and supplies it to the amplifier 16.

(c) The Amplifier 16

The amplifier 16 amplifies the detected signal outputted by the terahertz light detecting element 14 properly. And, the amplifier 16 supplies the detected signal amplified to the phase-amplitude comparator 32 of the network analyzer 18.

(d) The Network Analyzer 18

The network analyzer 18 includes a phase-amplitude comparator 32 for obtaining the phase or amplitude of the detected signal amplified by the amplifier 16 by using the reference signal generated by the high frequency reference signal source 20, an A/D converter 34 for converting analog signals obtained by the phase-amplitude comparator 32 into digital signals and a data processing block 36 for calculating the propagation characteristics of the object to be measured 10 based on the digital signals converted by the A/D converter 34.

The phase-amplitude comparator 32 obtains the phase or amplitude of the detected signal amplified by the amplifier 16 by using the reference signal generated by the high frequency reference signal source 20. The phase-amplitude comparator 32 outputs the comparison result in an analog signal form, and supplies it to the A/D converter 34.

The A/D converter 34 converts the analog signal outputted by the phase-amplitude comparator 32 into a digital signal form. The A/D converter 34 supplies the comparison result of a digital signal form to the data processing block 36.

The data processing block 36 calculates the propagation characteristics of the object to be measured 10 such as transmission attenuation amount or propagation delay by using the comparison result obtained by the phase-amplitude comparator 32.

(e) The High Frequency Reference Signal Source 20

The high frequency reference signal source 20 supplies the reference signal, an electrical signal of frequency $f_{IF}$, to the optical intensity modulator 26 of the modulated terahertz light source 12 and the phase-amplitude comparator 32 of the network analyzer 18. The optical intensity modulator 26, as described above, uses the reference signal generated by the high frequency reference signal source 20 when modulating the infrared light outputted from the infrared light source 24. The phase-amplitude comparator 32, as described above, uses the reference signal generated by the high frequency reference signal source 20 as a reference signal when comparing the phase or amplitude of the detected signal amplified by the amplifier 16.

The frequency $f_{IF}$ of the reference signal supplied to the optical intensity modulator 26 and the phase-amplitude comparator 32 from the high frequency reference signal source 20 is set to be enough lower than the frequency $f_2$ of the infrared light outputted from the infrared light source 24. The frequency $f_{IF}$ of the reference signal lower is, e.g. 1 GHz.

The propagation measuring apparatus 100 according to the present embodiment has two infrared light sources, i.e. the sweep type infrared light source 22 and the infrared light source 24, performs conversion of the infrared light outputted by the infrared light source 24 by the optical intensity modulator 26 and generates the modulated terahertz light by using the infrared light obtained in the way above.

Figure 9:
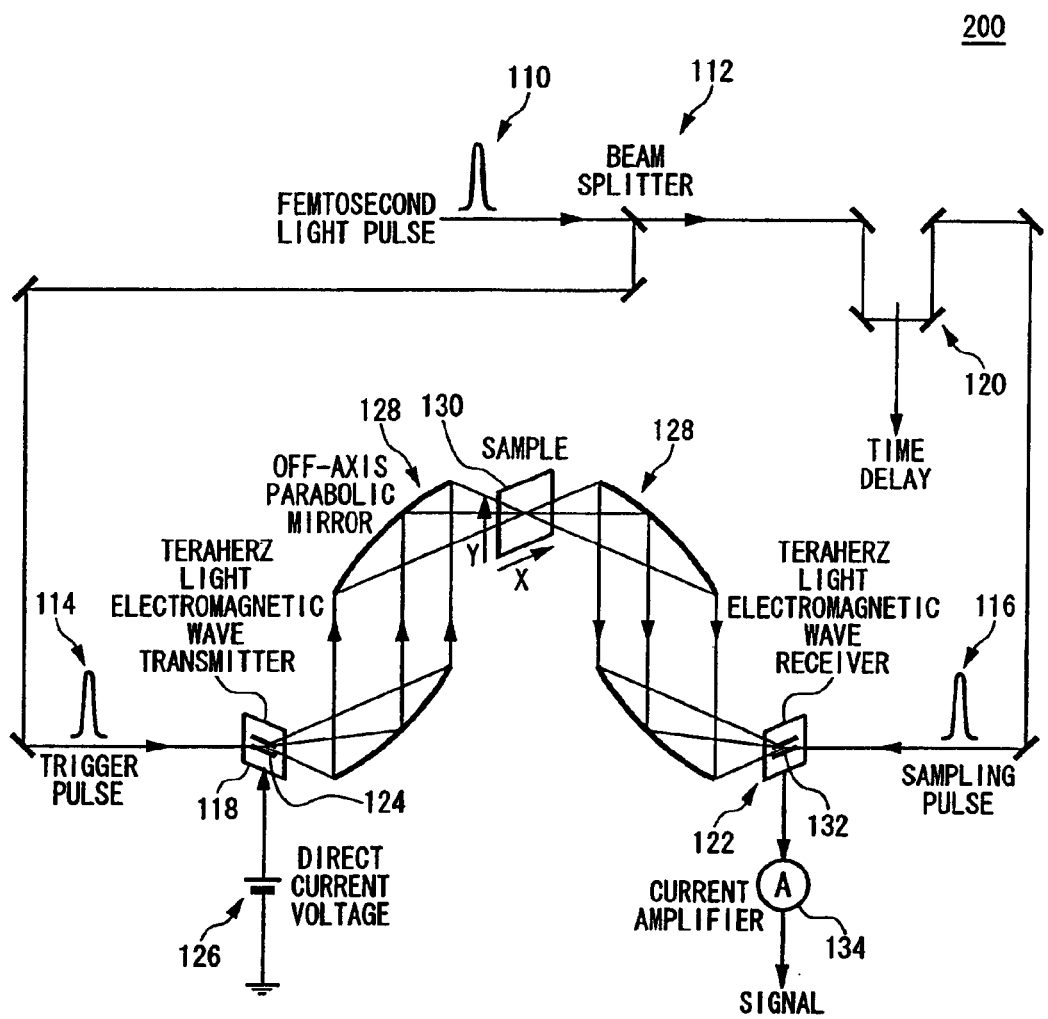
FIG. 9 shows a conventional propagation measuring apparatus 200 schematically.

In the propagation measuring apparatus 200 shown in FIG. 9, since the short pulse light is used to generate the terahertz light, the line width becomes wide. Therefore, the measurement precision becomes low as well as the resolution.

In contrast, in the propagation measuring apparatus 100 according to the present embodiment, since the terahertz light is generated by using the infrared light of continuous wave whose line width is narrow, it is possible to generate the terahertz light whose line width is narrow. Therefore, it is possible to measure the propagation characteristics with high precision and high resolution.

In addition, in the propagation measuring apparatus 200 shown in FIG. 9, since the measurement is performed while changing the delay time of the sampling pulse 116 gradually by using the time delay means 120, it takes a long time to perform the measurement.

In contrast, in the propagation measuring apparatus 10 according to the present embodiment, to perform the propagation measurement the frequency of the terahertz light outputted by the modulated terahertz light source 12 is changed by sweeping the frequency of the infrared light outputted by the sweep type infrared light source 22. Therefore, it is possible to measure the frequency dependency of the propagation characteristics of the object to be measured 10 at high speed and with high precision.

Figure 10:
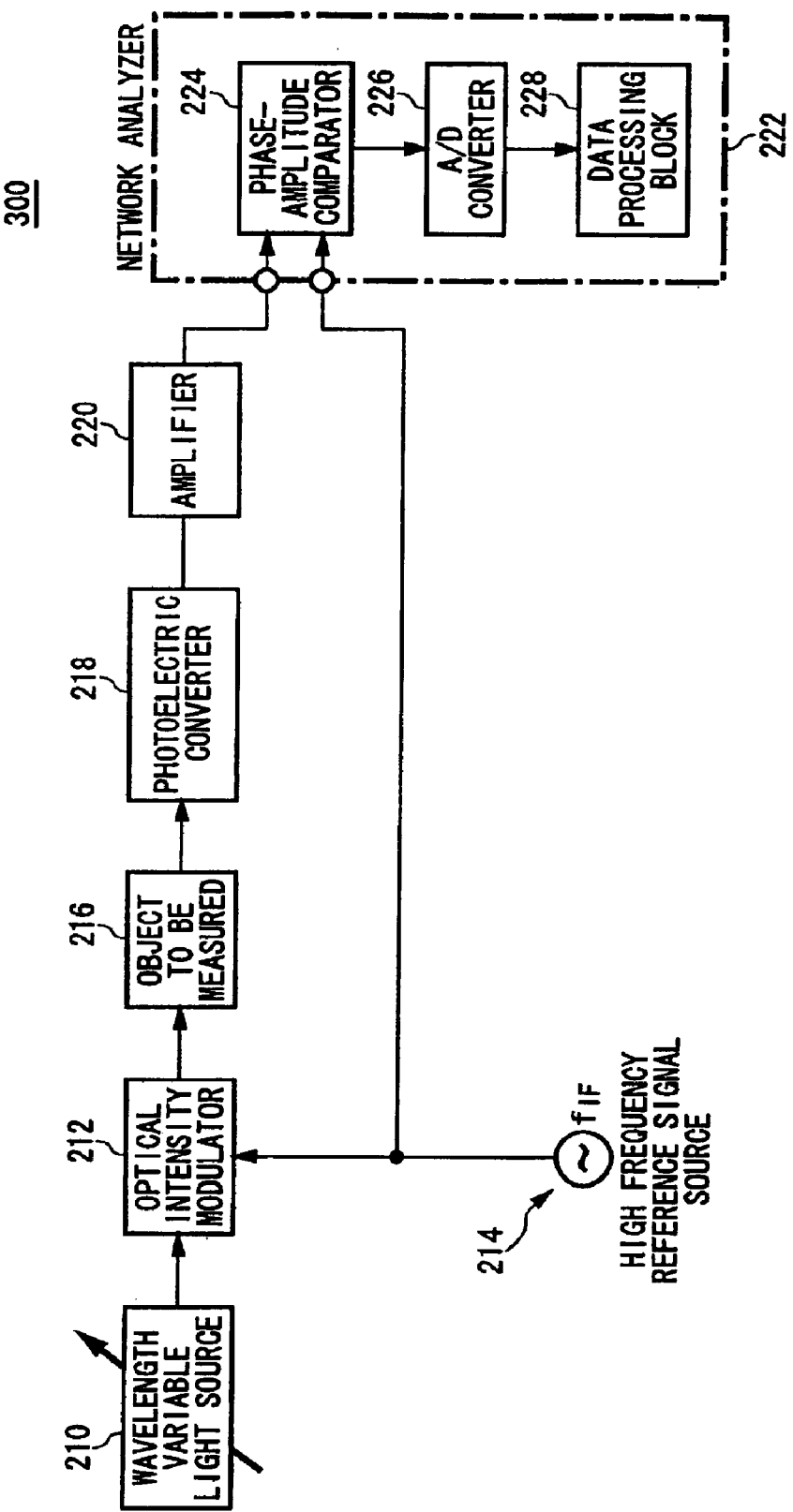
FIG. 10 shows a conventional wavelength dispersion measuring apparatus 300 schematically.
Figure 11:
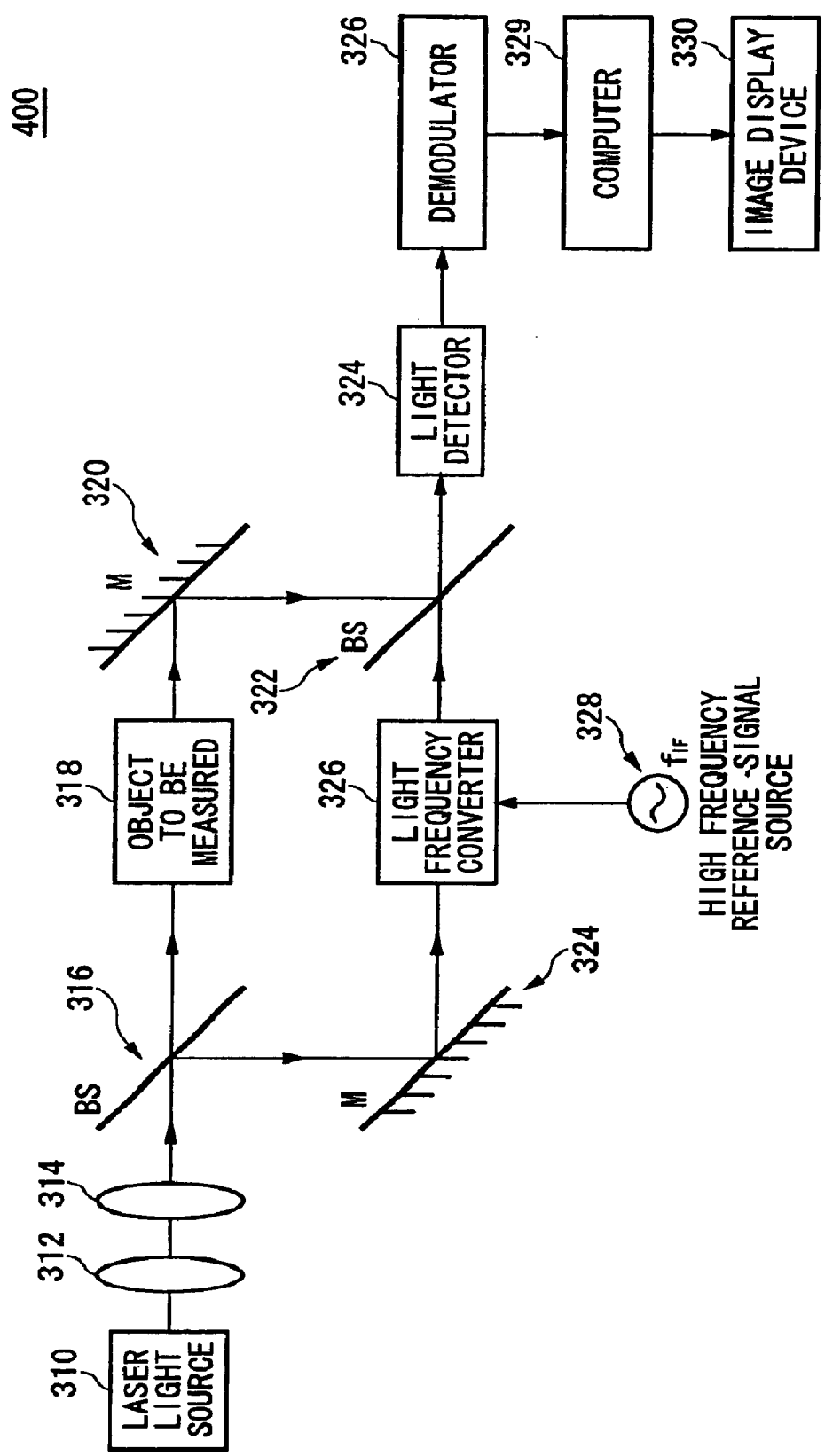
FIG. 11 shows a conventional apparatus for obtaining an optical tomographic image 400 schematically.

In case of applying the art of the wavelength dispersion measuring apparatus 300 shown in FIG. 10 to the terahertz light area simply, it is necessary to use a broadband optical intensity modulator of the terahertz light area as the optical intensity modulator 212. Since the broadband optical intensity modulator of the terahertz light area is not widely spread, it is difficult to procure it and its price is high.

In contrast, The propagation measuring apparatus 100 according to the present embodiment has two infrared light sources, i.e. the sweep type infrared light source 22 and the infrared light source 24, performs conversion of the infrared light outputted by the infrared light source 24 by the optical intensity modulator 26 and generates the modulated terahertz light by using the infrared light obtained in the way above. Therefore, it is possible to configure the modulated terahertz light source 12 by using the optical intensity modulator 26 of the narrowband infrared light area, wherein it is widely spread and easily procured, without using a broadband optical intensity modulator of the terahertz light area. Thus, it is possible to provide the propagation measuring apparatus 100 of the terahertz light area at a low cost.

In addition, in case of applying the art of the wavelength dispersion measuring apparatus 300 shown in FIG. 10 to the terahertz light area simply, the terahertz light outputted from the wavelength variable light source 210 is inputted into the photoelectric converter 218 via the optical intensity modulator 212 and the object to be measured 216. The transmission technique by which the loss in regard to the terahertz light area is low has not yet been progressed, it is necessary to make the intensity of the terahertz light outputted from the wavelength variable light source 210 large as much as the transmission loss. Therefore, it is necessary to use the wavelength variable light source 210 whose output is great, and thus it becomes an obstacle to making the apparatus small.

In contrast, in the propagation measuring apparatus 100 according to the present embodiment, since the path through which the terahertz light is propagated, is extremely short from the infrared light/terahertz light converting element 30 to the terahertz light detecting element 14, the loss in the propagation is small. Therefore, the modulated terahertz light source 12 can be configured without using a large light source, and thus it is possible to make the propagation measuring apparatus small.

As described above, according to the propagation measuring apparatus 100 of the present embodiment, it is possible to measure the propagation characteristics of the object to be measured 10 in regard to the terahertz light area with high precision and at high speed. Further, according to the present embodiment it is possible to provide the propagation measuring apparatus 100 with an easy configuration and at a low cost.

In the present embodiment, although a case of generating the terahertz light by using the infrared light, any light signal except the infrared light may be used. In other words, the modulated terahertz light source 12 may include a light source for outputting a light signal except the infrared light as an alternative to the sweep type infrared light source 22 and the infrared light source 24, and may include a converting element for converting optical signals except the infrared light into the terahertz light as an alternative to the infrared light/terahertz light converting element 30.

Figure 2:
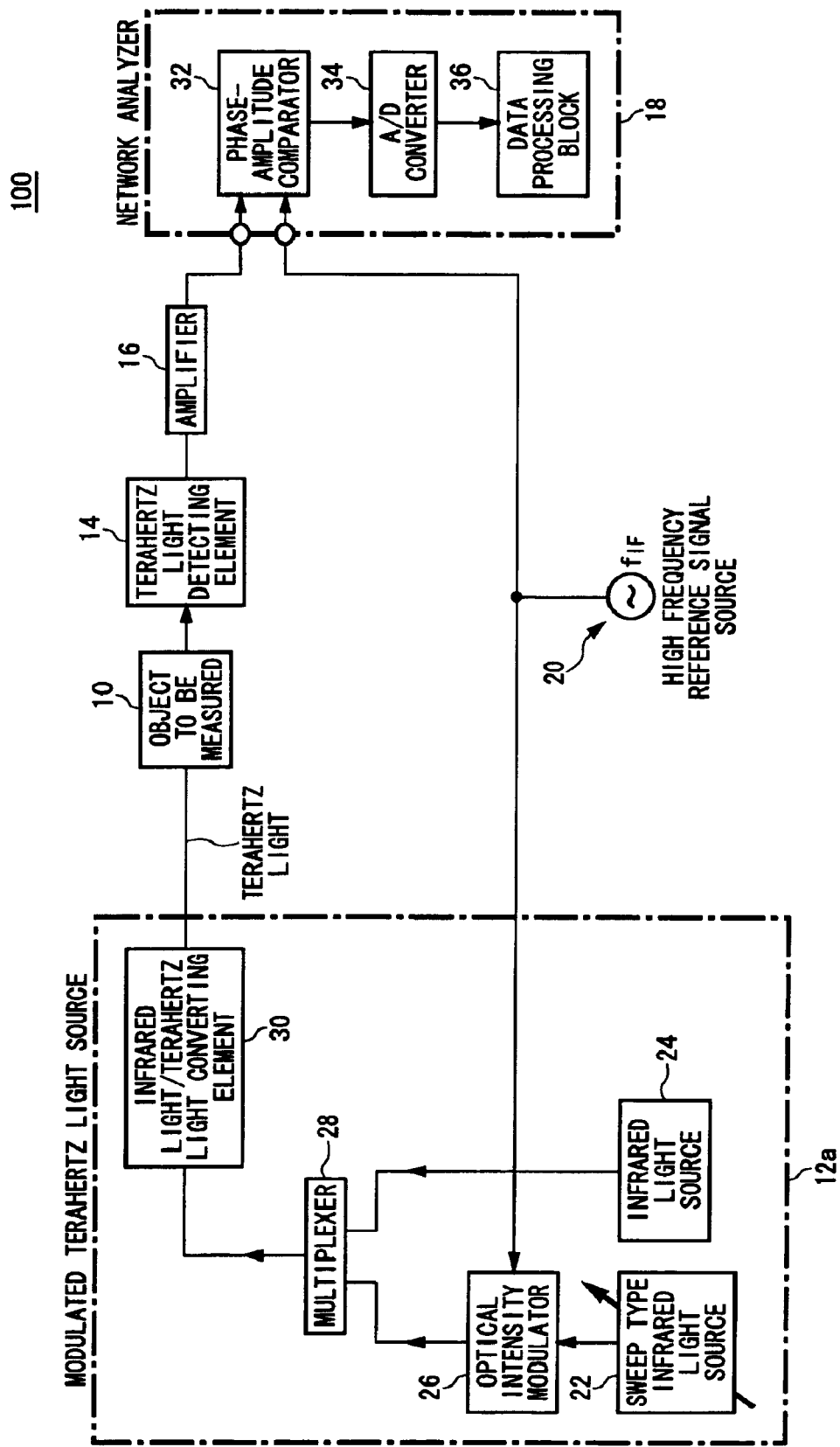
FIG. 2 shows a first modified example of the functional configuration of a propagation measuring apparatus 100 according to a first embodiment of the present invention.

FIG. 2 shows a first modified example of the functional configuration of a propagation measuring apparatus 100 according to a first embodiment of the present invention.

While the propagation measuring apparatus 100 shown in FIG. 1 has the optical intensity modulator 26 between the infrared light source 24 and the multiplexer 28, the propagation measuring apparatus 100 according to the present modified example has the optical intensity modulator 26 between the sweep type infrared light source 22 and the multiplexer 28.

Even if the optical intensity modulator 26 is provided between the sweep type infrared light source 22 and the multiplexer 28 as above, it is possible to configure a modulated terahertz light source 12a for outputting and obtaining the modulated terahertz light. Therefore, also in the present modified example it is possible to provide the propagation measuring apparatus 100 of a simple configuration at a low cost, wherein the propagation characteristics of the object to be measured in regard to the terahertz light area are measured and obtained with high precision and at high speed.

Figure 3:
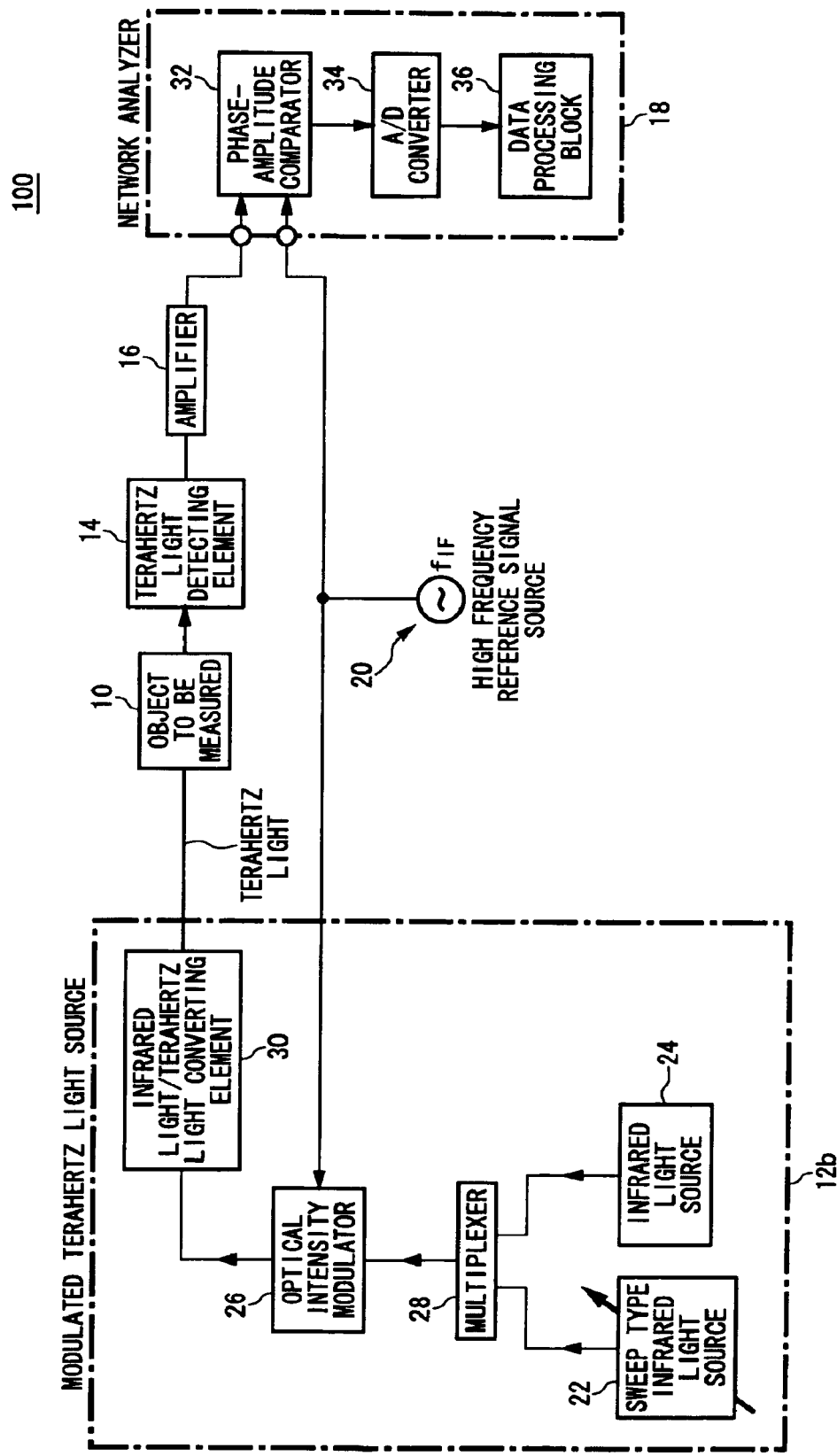
FIG. 3 shows a second modified example of the functional configuration of a propagation measuring apparatus 100 according to a first embodiment of the present invention.

FIG. 3 shows a second modified example of the functional configuration of a propagation measuring apparatus 100 according to a first embodiment of the present invention.

While the propagation measuring apparatus 100 shown in FIG. 1 has the optical intensity modulator 26 between the infrared light source 24 and the multiplexer 28, the propagation measuring apparatus 100 according to the present modified example has the optical intensity modulator 26 between the multiplexer 28 and the infrared light/terahertz light converting element 30. The optical intensity modulator 26 modulates the intensity of the infrared light multiplexed by the multiplexer 28. And, the infrared light/terahertz light converting element 30 generates the terahertz light by using the infrared light whose intensity is modulated by the optical intensity modulator 26.

Even if the optical intensity modulator 26 is provided between the multiplexer 28 and the infrared light/terahertz light converting element 30 as above, it is possible to configure a modulated terahertz light source 12b for outputting and obtaining the modulated terahertz light. Therefore, also in the present modified example it is possible to provide the propagation measuring apparatus 100 of a simple configuration at a low cost, wherein the propagation characteristics of the object to be measured in regard to the terahertz light area are measured and obtained with high precision and at high speed.

[Second Embodiment]

Figure 4:
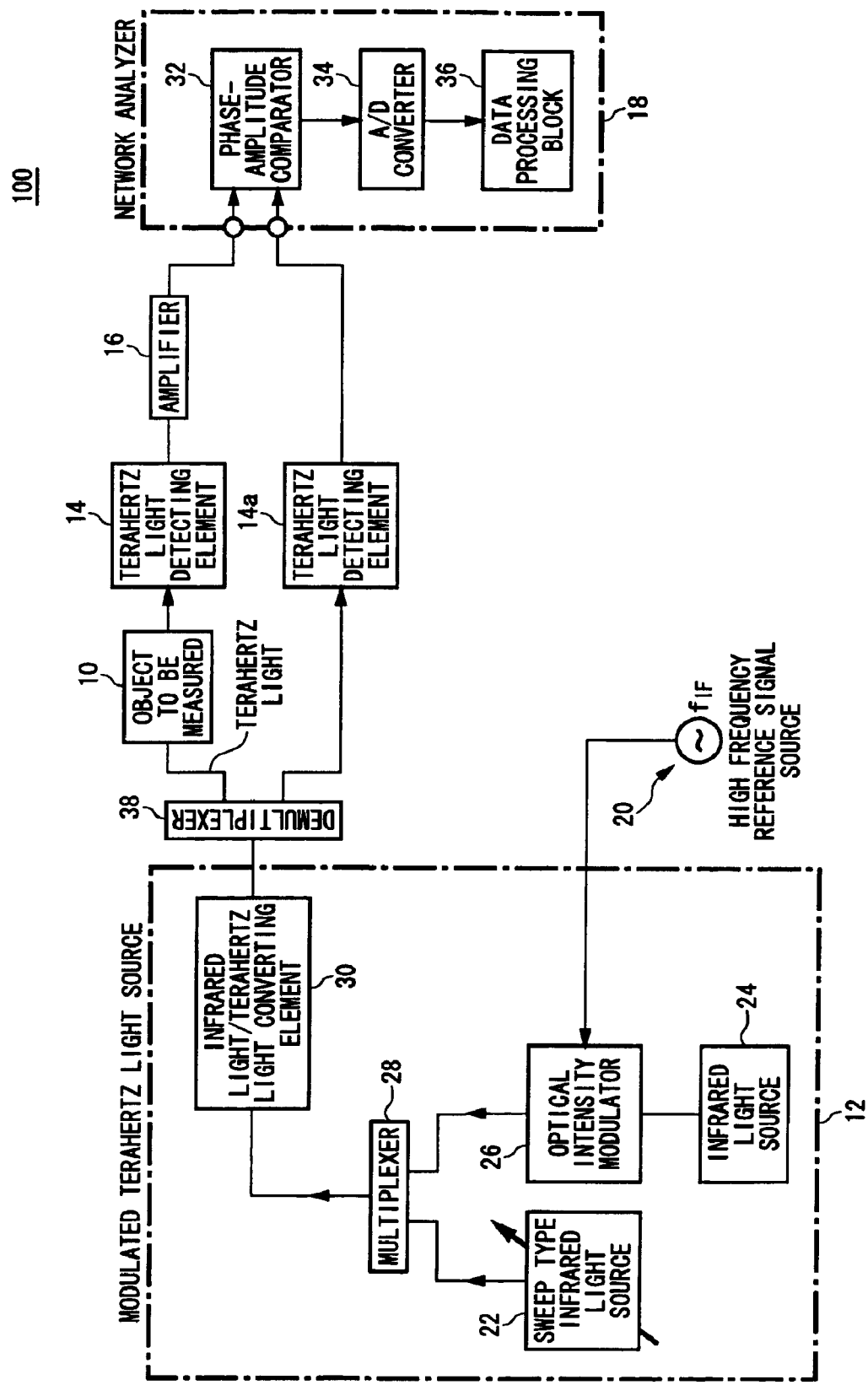
FIG. 4 shows an example of the functional configuration of a propagation measuring apparatus 100 according to a second embodiment of the present invention.

FIG. 4 shows an example of the functional configuration of a propagation measuring apparatus 100 according to a second embodiment of the present invention. In the second embodiment, the same elements as those of the propagation measuring apparatus 100 according to the first embodiment are given the same symbols and the description of those elements will be omitted or they will be described briefly.

The propagation measuring apparatus 100 according to the present embodiment, in addition to the propagation measuring apparatus 100 according to the first embodiment, includes a demultiplexer 38 for demultiplexing the terahertz light radiated by the infrared light/terahertz light converting element 30 and a terahertz light detecting element 14a that an example of a second detecting unit for detecting the terahertz light radiated by the infrared light/terahertz light converting element 30 not through the object to be measured 10. As the terahertz light detecting element 14a, a device such as the terahertz light detecting element 14 can be used.

The terahertz light detecting element 14 detects one of two components of the terahertz light demultiplexed by the demultiplexer 38 via the object to be measured 10 and supplies the detected signal to the amplifier 16. And, the amplifier 16 amplifies the detected signal obtained by the terahertz light detecting element 14 and supplies it to the phase-amplitude comparator 32 of the network analyzer 18.

The terahertz light detecting element 14a detects the other component of the terahertz light demultiplexed by the demultiplexer 38 not through the object to be measured 10 and supplies the detected signal to the phase-amplitude comparator 32 of the network analyzer 18.

The phase-amplitude comparator 32 obtains the phase or amplitude of the detected signal based on the terahertz light detected by the terahertz light detecting element 14 taking the detected signal based on the terahertz light detected by the terahertz light detecting element 14a as the reference signal.

Since the phase-amplitude comparator 32 uses the signal generated by the high frequency reference signal source 20 as the reference signal in the propagation measuring apparatus 100 of the first embodiment, if the intensity of the terahertz light outputted by the infrared light/terahertz light converting element 30 is changed, the magnitude of the detected signal is changed against the magnitude of the reference signal as the reference of the comparison by the phase-amplitude comparator 32. Accordingly, in the propagation measuring apparatus 100 of the first embodiment, when the intensity of the terahertz light outputted by the infrared light/terahertz light converting element 30 is changed, there might be an error in the comparison by the phase-amplitude comparator 32.

In contrast, in the propagation measuring apparatus 100 according to the present embodiment, since the reference signal is generated by using the terahertz light outputted by the infrared light/terahertz light converting element 30, if the intensity of the terahertz light outputted by the infrared light/terahertz light converting element 30 is changed, the magnitude of the detected signal supplied to the phase-amplitude comparator 32 and the magnitude of the reference signal are changed in the same way. Therefore, it is possible to measure the propagation characteristics of the object to be measured 10 with high precision without being affected by the change in the intensity of the terahertz light outputted by the infrared light/terahertz light converting element 30.

[Third Embodiment]

Figure 5:
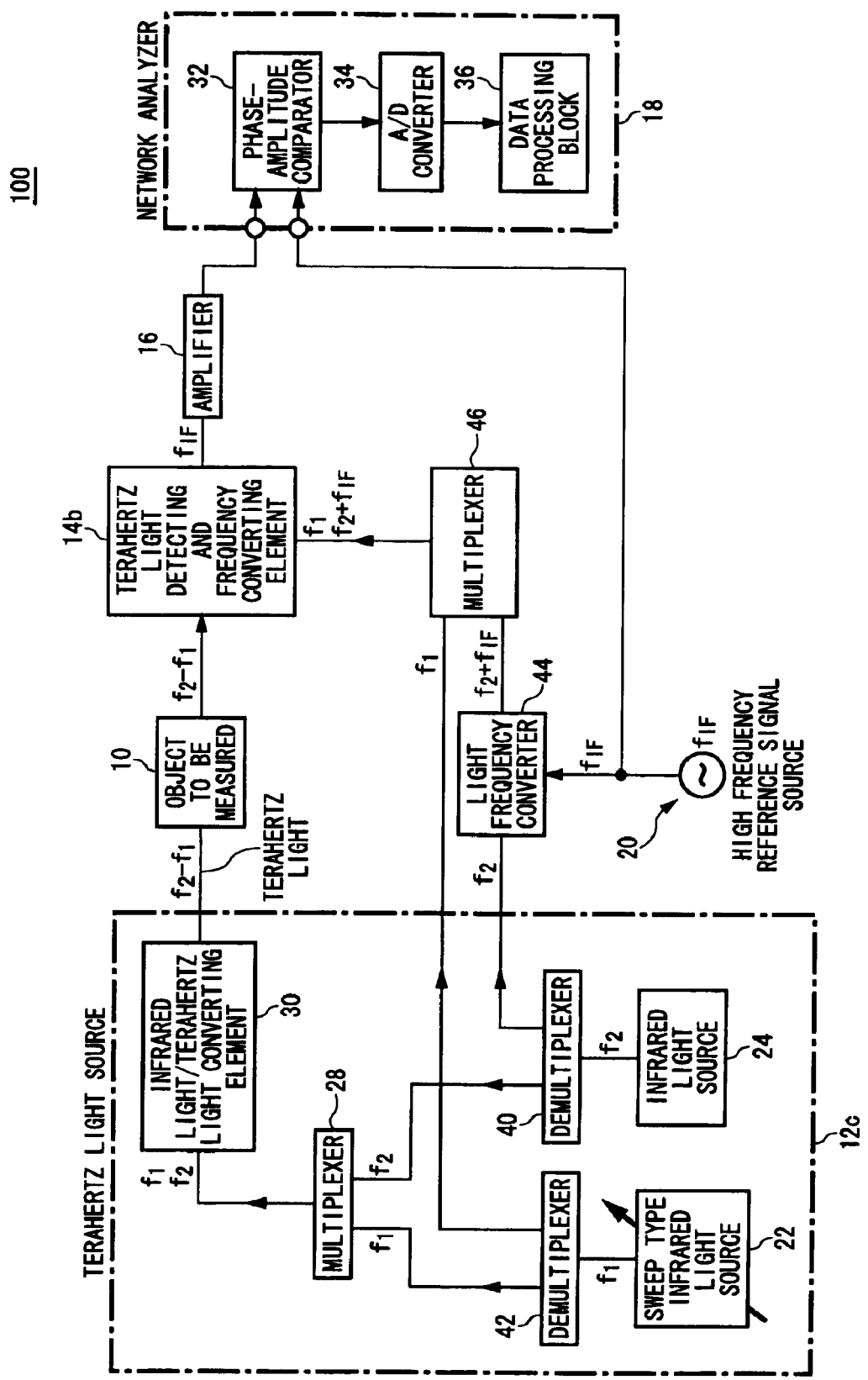
FIG. 5 shows an example of the functional configuration of a propagation measuring apparatus 100 according to a third embodiment of the present invention.

FIG. 5 shows an example of the functional configuration of a propagation measuring apparatus 100 according to a third embodiment of the present invention. In the third embodiment, the same elements as those of the propagation measuring apparatus 100 according to the first or second embodiment are given the same symbols and the description of those elements will be omitted or they will be described briefly.

The propagation measuring apparatus 100 according to the present embodiment includes a terahertz light source 12c for radiating terahertz light to the object to be measured 10, a light frequency converter 44 that is an example of a modulating unit for converting the frequency of the infrared light outputted out of the terahertz light source 12c from the infrared light source 24 via the demultiplexer 40 by using the reference signal generated by the high frequency reference signal source 20, a multiplexer 46 for multiplexing the infrared light outputted out of the terahertz light source 12c from the sweep type infrared light source 22 via the demultiplexer 42 and the infrared light whose frequency is converted by the frequency converter 44, a terahertz light detecting and frequency converting element 14b that is an example of a first detecting unit for performing heterodyne detection of the terahertz light passing through the object to be measured 10 by using the infrared light multiplexed by the multiplexer 46, an amplifier 16 for amplifying the detected signal detected by the terahertz light detecting and frequency converting element 14b, a network analyzer 18 that is an example of a measuring unit for analyzing the detected signal amplified by the amplifier 16 and measuring the propagation characteristics of the object to be measured 10 and a high frequency reference signal source 20 that is an example of a reference signal source for supplying the reference signal to the light frequency converter 44 and the network analyzer 18.

Hereinafter, each element of the propagation measuring apparatus 100 according to the present embodiment will be described in detail.

(a) The Terahertz Light Source 12c

The terahertz light source 12c includes a sweep type infrared light source 22 that is an example of a first light source for outputting the infrared light of frequency $f_1$, a demultiplexer 42 for demultiplexing the infrared light outputted by the sweep type infrared light source 22, an infrared light source 24 that is an example of a second light source for outputting the infrared light of frequency $f_2$, a demultiplexer 40 for demultiplexing the infrared light outputted by the infrared light source 24, a multiplexer 28 for multiplexing one of two components of the infrared light demultiplexed by the demultiplexer 42 and one of two components of the infrared light demultiplexed by the demultiplexer 40 and an infrared light/terahertz light converting element 30 that is an example of a terahertz light outputting unit for generating terahertz light and radiating it to the object to be measured 10 by using the infrared light multiplexed by the multiplexer 28.

The infrared light/terahertz light converting element 30 generates the terahertz light of the frequency $f_2-f_1$ and radiates it to the object to be measured 10 by using the infrared light of frequency $f_1$ outputted by the sweep type infrared light source 22 and the infrared light of frequency $f_2$ outputted by the infrared light source 24.

The terahertz light source 12c outputs the other component of the infrared light of frequency $f_1$ outputted by the sweep type infrared light source 22 and demultiplexed by the demultiplexer 42. The infrared light outputted out of the terahertz light source 12c from the sweep type infrared light source 22 via the demultiplexer 42 is supplied to the multiplexer 46.

The terahertz light source 12c outputs the other component of the infrared light frequency $f_2$ outputted by the infrared light source 24 and demultiplexed by the demultiplexer 40. The infrared light outputted out of the terahertz light source 12c from the sweep type infrared light source 22 via the demultiplexer 40 is supplied to the light frequency converter 44.

(b) The Light Frequency Converter 44

The light frequency converter 44 converts the frequency of the other component of the infrared light outputted by the infrared light source 24 and demultiplexed by the demultiplexer 40 by using the reference signal generated by the high frequency reference signal source 20. The light frequency converter 44 performs frequency conversion by using the reference signal generated by the high frequency reference signal source 20, and outputs the infrared light of frequency $f_2+f_{IF}$ or $f_2-f_{IF}$ and supplies it to the multiplexer 46.

(c) The Multiplexer 46

The multiplexer 46 multiplexes the other component of the infrared light outputted by the sweep type infrared light source 22 and demultiplexed by the demultiplexer 42 and the infrared light whose frequency is converted by the light frequency converter 44, and supplies it to the terahertz light detecting and frequency converting element 14b.

(d) The Terahertz Light Detecting and Frequency Converting Element 14b

The terahertz light detecting and frequency converting element 14b performs the heterodyne detection of the terahertz light passing through the object to be measured 10 by using the infrared light multiplexed by the multiplexer 46. The terahertz light of frequency $f_2-f_1$ passing through the object to be measured 10, the infrared light of frequency $f_1$ outputted by the multiplexer 46 and the infrared light of frequency $f_2+f_{IF}$ or $f_2-f_{IF}$ is inputted into the terahertz light detecting and frequency converting element 14b.

The beat frequency caused by the terahertz light of frequency $f_2-f_1$, the infrared light of frequency $f_1$ and the infrared light of frequency $f_2+f_{IF}$ inputted into the terahertz light detecting and frequency converting element 14b becomes:

$$(f_2-f_1)+(f_2+f_{IF})-f_1=f_{IF}.$$

The terahertz light detecting and frequency converting element 14b performs the heterodyne detection, wherein electronics follow the beat frequency $f_{IF}$. In other words, the terahertz light detecting and frequency converting element 14b performs the heterodyne detection taking the terahertz light of frequency $f_2-f_1$, the infrared light of frequency $f_1$ and the infrared light of frequency $f_2+f_{IF}$ as an input signal and taking the detected signal of as frequency $f_{IF}$ an output signal.

The intensities of the infrared light of frequency $f_1$ and the infrared light of frequency $f_2+f_{IF}$ multiplexed by the multiplexer 46 and supplied to the terahertz light detecting and frequency converting element 14b is enough higher than that of the terahertz light of frequency $f_2-f_1$ passing through the object to be measured 10 and detected by the terahertz light detecting and frequency converting element 14b. Therefore, by using the infrared light whose intensity is enough higher than that of the terahertz light, the heterodyne detection can be performed and it is possible to detect the minute terahertz light around the shot noise limit.

As described above, according to the propagation measuring apparatus 100 of the present embodiment, since the heterodyne detection of the terahertz light can be performed, it is possible to measure the propagation characteristics of the object to be measured 10 with higher sensitivity.

While the propagation measuring apparatus 100 according to the present embodiment has the light frequency converter 44 between the demultiplexer 40 and the multiplexer 46, the place at which the light frequency converter 44 is positioned is not limited between the demultiplexer 40 and the multiplexer 46, and, e.g. maybe between the demultiplexer 42 and the multiplexer 46, the demultiplexer 42 and the multiplexer 28 or the demultiplexer 40 and the multiplexer 28.

Figure 6:
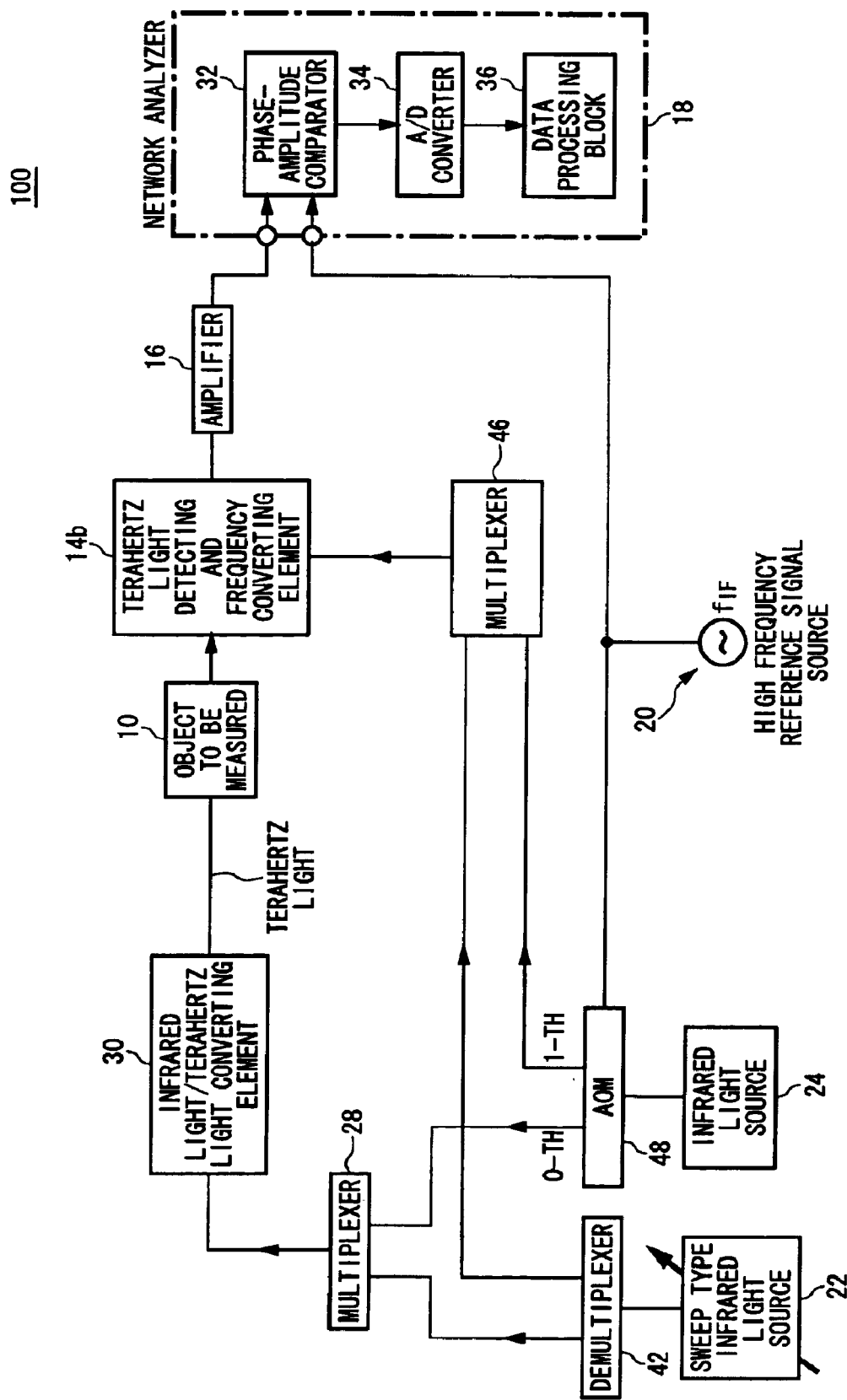
FIG. 6 shows a first modified example of the functional configuration of a propagation measuring apparatus 100 according to a third embodiment of the present invention.

FIG. 6 shows a first modified example of the functional configuration of a propagation measuring apparatus 100 according to the third embodiment of the present invention.

The propagation measuring apparatus 100 according to the present modified example, in addition to the demultiplexer 40 and the light frequency converter 44 of the propagation measuring apparatus 100 shown in FIG. 5, includes an AOM (Acousto-Optic Modulator, an acousto-optic converter) 48. The AOM 48 is an optical modulator using acousto-optic diffraction.

The AOM 48 converts the frequency $f_2$ of the infrared light outputted by the infrared light source. The AOM 48 outputs the infrared light supplied from the infrared light source 24 at the 0-th order side without changing the frequency, and supplies it to the multiplexer 28. The AOM 48 changes the frequency of the infrared light supplied from the infrared light source 24, outputs it at the 1-th order side, and supplies it to the multiplexer 46.

In the propagation measuring apparatus 100 shown in FIG. 5, since the demultiplexer 40 demultiplexes the infrared light outputted by the infrared light source 24 and the light frequency converter 44 converts the frequency of the infrared light demultiplexed by the demultiplexer 40, the number of the configuration elements becomes large.

In contrast, since the propagation measuring apparatus 100 according to the present modified example includes the AOM 48 having the demultiplexing function and the frequency conversion function, the number of the configuration elements can be reduced. Therefore, the configuration of the propagation measuring apparatus 100 can be simple, and thus it can be small and inexpensive.

In addition, while the 0-th order side of the AOM 48 is coupled to the multiplexer 28 and the 1-th order side of the AOM 48 is coupled to the multiplexer 46 in the propagation measuring apparatus 100 according to the present modified example, the 0-th order side of the AOM 48 may be coupled to the multiplexer 46 and the 1-th order side of the AOM 48 may be coupled to the multiplexer 28. In addition, while the AOM 48 is provided between the infrared light source 24 and the multiplexer 28 in the propagation measuring apparatus 100 according to the present modified example, the AOM 48 may be provided between the sweep type infrared light source 22 and the multiplexer 28. In this case, a demultiplexer may be provided between the infrared light source 24 and the multiplexer 28.

Figure 7:
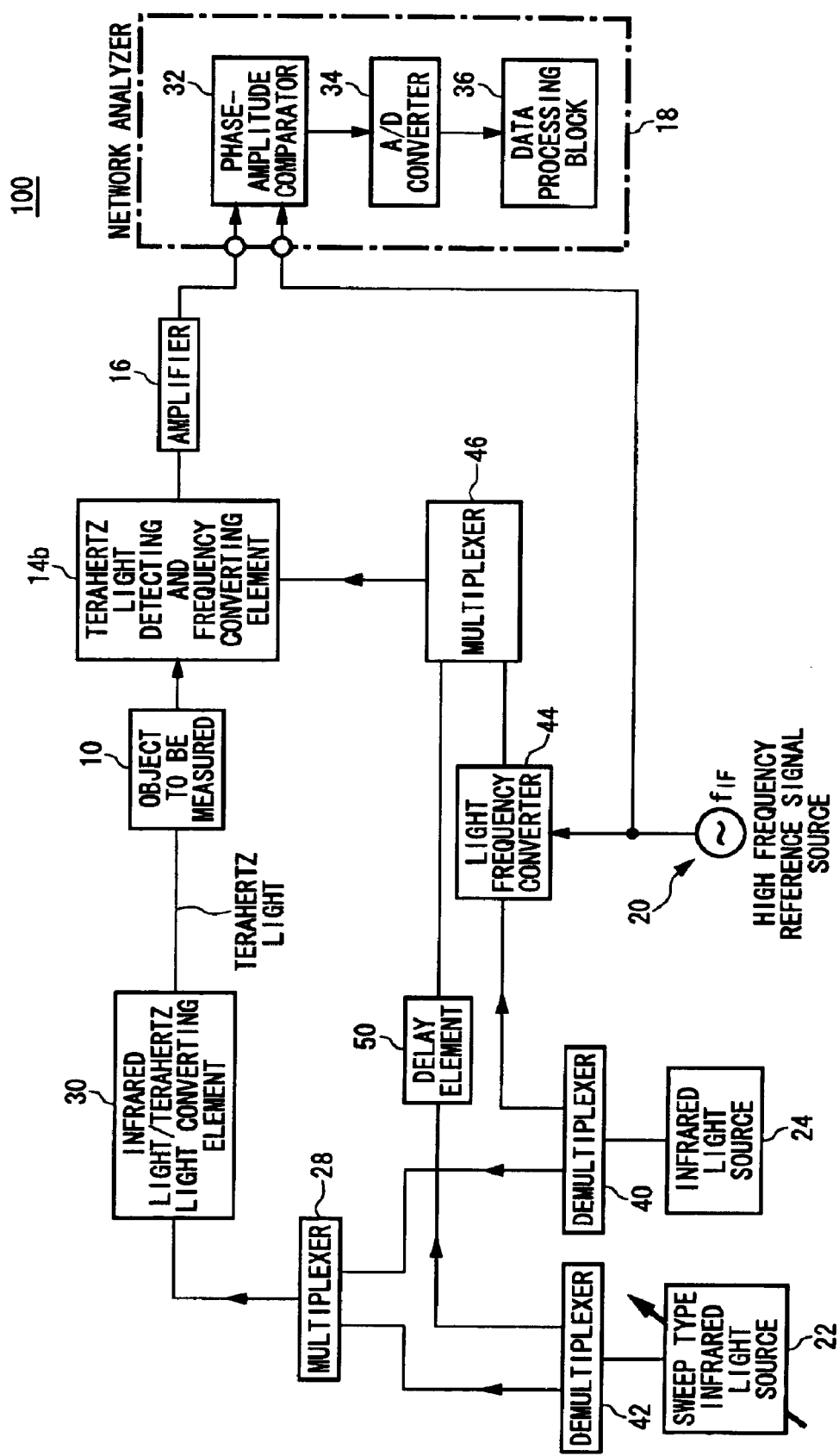
FIG. 7 shows a second modified example of the functional configuration of a propagation measuring apparatus 100 according to a third embodiment of the present invention.

FIG. 7 shows a second modified example of the functional configuration of a propagation measuring apparatus 100 according to the third embodiment of the present invention.

The propagation measuring apparatus 100 according to the present modified example further includes a delay element 50 between the demultiplexer 42 and the multiplexer 46. The delay element 50 delays the time until the infrared light demultiplexed by the demultiplexer 42 reaches the terahertz light detecting and frequency converting element 14b.

By the delay element 50, it is possible to match a delay time $T_1$ until the infrared light demultiplexed by the demultiplexer 42 reaches the terahertz light detecting and frequency converting element 14b via the multiplexer 28, the infrared light/terahertz light converting element 30 and the object to be measured 10 in the terahertz light form and a delay time $T_2$ until it reaches the terahertz light detecting and frequency converting element 14b via the delay element 50 and the multiplexer 46 in the infrared light form.

If the delay time $T_1$ and the delay time $T_2$ do not match, when the infrared light of frequency $f_1$ outputted by the sweep type infrared light source 22 is swept, there is a difference between the timing at which the frequency of the terahertz light detected by the terahertz light detecting and frequency converting element 14b and the timing at which the frequency of the infrared light supplied to the terahertz light detecting and frequency converting element 14b, so that the measurement error occurs.

In contrast, since the propagation measuring apparatus 100 according to the present modified example has the delay element 50 between the demultiplexer 42 and the multiplexer 46, it is possible to match the delay time $T_1$ and the delay time $T_2$. Therefore, even if the infrared light of frequency $f_1$ outputted by the sweep type infrared light source 22 is swept, it is possible to prevent the measurement error caused by sweeping the frequency $f_1$ of the infrared light from occurring. Thus, according to the present modified example, it is possible to measure the frequency dependency of the propagation characteristics with higher precision and at higher speed.

[Fourth Embodiment]

Figure 8:
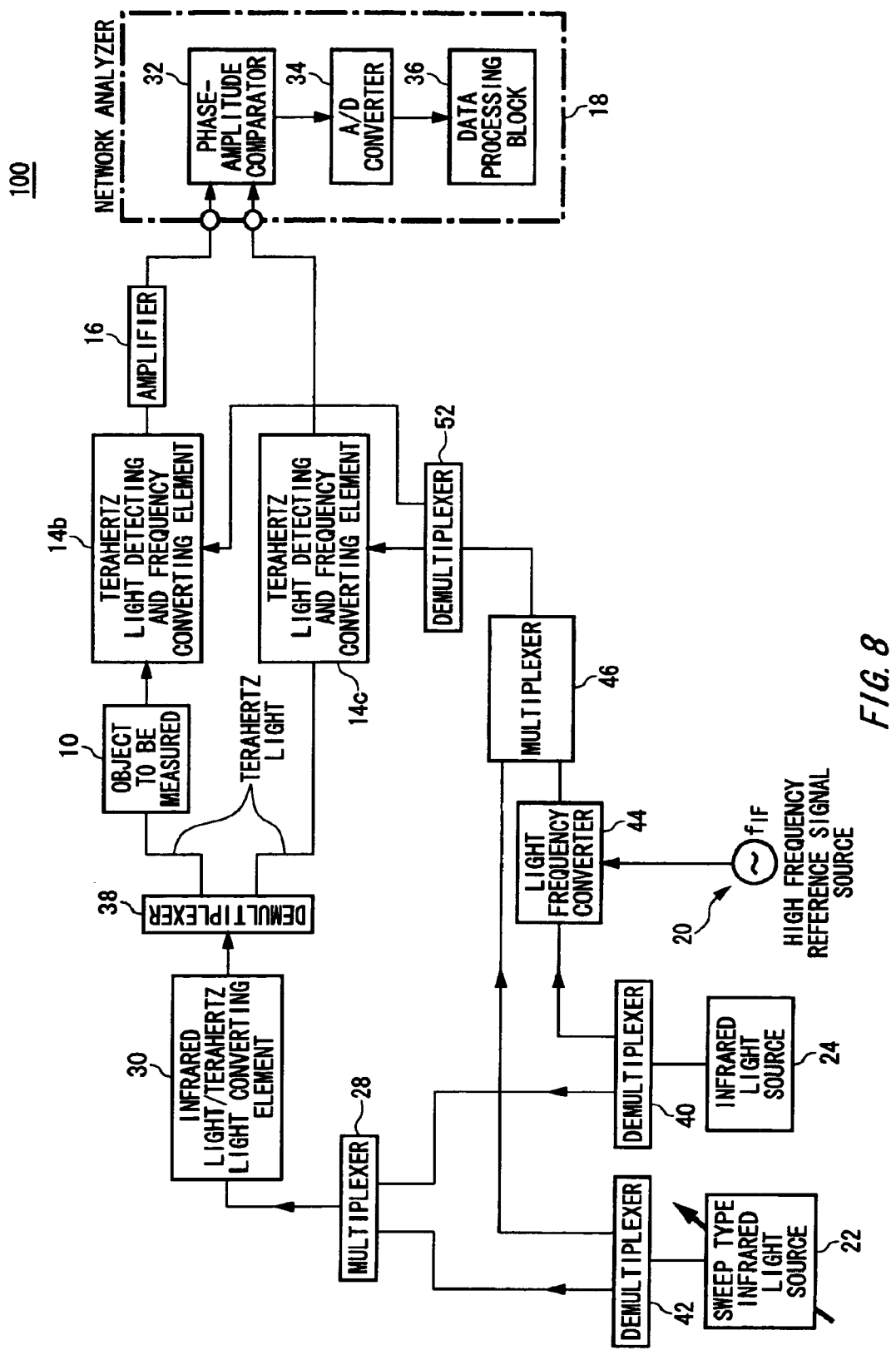
FIG. 8 shows an example of the functional configuration of a propagation measuring apparatus 100 according to a fourth embodiment of the present invention.

FIG. 8 shows an example of the functional configuration of a propagation measuring apparatus 100 according to a fourth embodiment of the present invention. In the third embodiment, the same elements as those of the propagation measuring apparatus 100 according to the first, second or third embodiment are given the same symbols and the description of those elements will be omitted or they will be described briefly.

The propagation measuring apparatus 100 according to the present embodiment, in addition to the propagation measuring apparatus 100 according to the third embodiment, includes a demultiplexer 38 for demultiplexing the terahertz light radiated by the infrared light/terahertz light converting element 30, a demultiplexer 52 for demultiplexing the infrared light multiplexed by the multiplexer 46 and a terahertz light detecting and frequency converting element 14c that is an example of a second detecting unit for detecting the terahertz light radiated by the infrared light/terahertz light converting element 30 not through the object to be measured 10 and performing the heterodyne detection by using the infrared light demultiplexed by the demultiplexer 52. As the terahertz light detecting and frequency converting element 14c, a device such as the terahertz light detecting and frequency converting element 14b may be used.

The terahertz light detecting and frequency converting element 14b detects one of two components of the terahertz light demultiplexed by the demultiplexer 38 via the object to be measured 10, and performs the heterodyne detection by using one of two components of the infrared light demultiplexed by the demultiplexer 52. And, the terahertz light detecting and frequency converting element 14b supplies the detected signal that is the result of the heterodyne detection to the amplifier 16. The amplifier 16 amplifies the detected signal obtained by the terahertz light detecting and frequency converting element 14b and supplies it to the phase-amplitude comparator 32 of the network analyzer 18.

The terahertz light detecting and frequency converting element 14c detects the other component of the terahertz light demultiplexed by the demultiplexer 38 not through the object to be measured 10, and performs the heterodyne detection by using the other component of the infrared light demultiplexed by the demultiplexer 52. And, the terahertz light detecting and frequency converting element 14c supplies the detected signal that is the result of the heterodyne detection to the phase-amplitude comparator 32 of the network analyzer 18.

The phase-amplitude comparator 32 obtains the phase or amplitude of the detected signal based on the terahertz light detected by the terahertz light detecting and frequency converting element 14b taking the detected signal based on the terahertz light detected by the terahertz light detecting and frequency converting element 14c as the reference signal.

In the propagation measuring apparatus 100 according to the third embodiment, since the phase-amplitude comparator 32 uses the signal generated by the high frequency reference signal source 20 as the reference signal, if the intensity of the terahertz light outputted by the infrared light/terahertz light converting element 30 is changed, the magnitude of the detected signal is changed against the magnitude of the reference signal that is a criterion of the comparison by the phase-amplitude comparator 32. Therefore, in the propagation measuring apparatus 100 according to the third embodiment, if the intensity of the terahertz light outputted by the infrared light/terahertz light converting element 30 is changed, there might be an error in the comparison result conducted by the phase-amplitude comparator 32.

In contrast, in the propagation measuring apparatus 100 according to the present embodiment, since the terahertz light outputted by the infrared light/terahertz light converting element 30 is used to generate the reference signal, if the intensity of the terahertz light outputted by the infrared light/terahertz light converting element 30 is changed, the magnitude of the detected signal and the magnitude of the reference signal supplied to the phase-amplitude comparator 32 are changed in the same way. Therefore, it is possible to measure the propagation characteristics of the object to be measured 10 with high precision without being affected by the change in the intensity of the terahertz light outputted by the infrared light/terahertz light converting element 30.

The propagation measuring apparatus 100 according to the present invention is not limited to the previous embodiments and may be modified variously. For example, in regard to the propagation measuring apparatus 100 according to the previous embodiments, a filter of intermediate frequency $f_{IF}$ may be inserted between the terahertz light detecting element 14 or 14a and the phase-amplitude comparator 32 or the terahertz light detecting and frequency converting element 14b or 14c and the phase-amplitude comparator 32. Accordingly, the noise can be eliminated and it is possible to improve the measurement precision.

Although the present invention has been described by way of exemplary embodiments, it should be understood that those skilled in the art might make many changes and substitutions without departing from the spirit and the scope of the present invention, which is defined only by the appended claims.

As obvious from the description above, according to the present invention, it is possible to provide a propagation measuring apparatus and a propagation measuring method capable of measuring and obtaining the propagation characteristics of an object to be measured in regard to the terahertz light area. Further, it is possible to provide the propagation measuring apparatus as above with a simple configuration and at a low cost.

What is claimed is:

1. A propagation measuring apparatus for measuring propagation characteristics of an object to be measured comprising:

a first light source for outputting a first optical signal of a first frequency;

a second light source for outputting a second optical signal of a second frequency;

a terahertz light outputting unit for generating terahertz light of a frequency, which is equal to a difference between said first and second frequencies, by using said first and second optical signals and radiating said terahertz light to said object to be measured:

a first detecting unit for detecting said terahertz light passing through said object to be measured;

a measuring unit for measuring said propagation characteristics of said object to be measured based on said terahertz light detected by said first detecting unit;

a reference signal source for generating a referencee signal; and a modulating unit for modulating at least one of said first and second optical signals based on said reference signal generated by said reference signal source, wherein said measuring unit measures said propagation characteristics of said object to be measured based on at least one of said first and second optical signals modulated by said modulating unit and said reference signal generated by said reference signal source, further comprising:

a first demultiplexer for demultiplexing said first optical signal outputted by said first light source;

a second demultiplexer for demultiplexing said second optical signal outputted by said second light source;

a first multiplexer for multiplexing a first component of said first optical signal demultiplexed by said first demultiplexer and a first component of said second optical signal demultiplexed by said second demultiplexer; and a second multiplexer for multiplexing a second component of said first optical signal demultiplexed by said first demultiplexer and a second component of said second optical signal demultiplexed by said second demultiplexer, wherein said terahertz light outputting unit generates said terahertz light by using said first and second optical signals multiplexed by said first multiplexer and radiates said terahertz light to said object to be measured, said modulating unit modulates a frequency of said second component of said first optical signal demultiplexed by said first demultiplexer, said second multiplexer multiplexes said second component of said first optical signal of which said frequency is odulated by said modulating unit and said second component of said second optical signal demultiplexed by said second demultiplexer, and said first detecting unit performs heterodyne detection of said terahertz light passing through said object to be measured by using said second components of said first and second optical signals multiplexed by said second multiplexer.

2. A propagation measuring apparatus as claimed in claim 1 further comprising a delay element for delaying at least one of said second component of said first optical signal demultiplexed by said first demultiplexer and said second component of said second optical signal demultiplexed by said second demultiplexer.

3. A propagation measuring apparatus as claimed in claim 1 further comprising a second detecting unit for detecting said terahertz light radiated by said terahertz light outputting unit not through said object to be measured and performing heterodyne detection by using said second components of said first and second optical signals multiplexed by said second multiplexer, wherein said measuring unit measures said propagation characteristics of said object to be measured based on results of said heterodyne detection of said first and second detecting units.

* * * * *